(12) United States Patent
Moberg

(10) Patent No.: US 6,248,093 B1
(45) Date of Patent: Jun. 19, 2001

(54) COMPACT PUMP DRIVE SYSTEM

(75) Inventor: Sheldon Moberg, Granada Hills, CA (US)

(73) Assignee: MiniMed Inc., Northridge, CA (US)

( * ) Notice: Subject to any disclaimer, the term of this patent is extended or adjusted under 35 U.S.C. 154(b) by 0 days.

(21) Appl. No.: 09/429,352

(22) Filed: Oct. 28, 1999

Related U.S. Application Data

(60) Provisional application No. 60/106,237, filed on Oct. 29, 1998.

(51) Int. Cl.[7] .................................................. A61M 5/00
(52) U.S. Cl. .................. 604/131; 604/151; 128/DIG. 12
(58) Field of Search .................................. 604/131, 151, 604/154, 155; 128/DIG. 1, DIG. 12, DIG. 13

(56) References Cited

U.S. PATENT DOCUMENTS

| | | |
|---|---|---|
| D. 347,894 | 6/1994 | Hansen et al. . |
| D. 380,262 | 6/1997 | Van Funderburk et al. . |
| 3,623,474 | 11/1971 | Heilman et al. . |
| 3,701,345 | 10/1972 | Heilman et al. . |
| 4,084,588 | 4/1978 | Koenig . |
| 4,267,836 | 5/1981 | Whitney et al. . |
| 4,444,546 | 4/1984 | Pazemenas . |
| 4,468,221 | 8/1984 | Mayfield . |
| 4,562,751 | 1/1986 | Nason et al. . |
| 4,576,211 | 3/1986 | Valentini et al. . |
| 4,601,491 | 7/1986 | Bell, Jr. et al. . |
| 4,619,646 | 10/1986 | Hernandez et al. . |
| 4,678,408 | 7/1987 | Nason et al. . |
| 4,685,903 | 8/1987 | Cable et al. . |
| 4,744,790 | 5/1988 | Jankowski et al. . |
| 4,747,824 | 5/1988 | Spinello . |
| 4,749,109 | 6/1988 | Kamen . |
| 4,952,205 | 8/1990 | Mauerer et al. . |
| 5,080,653 | 1/1992 | Voss et al. . |
| 5,097,122 | 3/1992 | Colman et al. . |
| 5,121,019 | 6/1992 | Pradler . |
| 5,219,099 | 6/1993 | Spence et al. . |
| 5,254,096 | 10/1993 | Rondelet et al. . |
| 5,292,306 | 3/1994 | Wynkoop et al. . |
| 5,389,078 | 2/1995 | Zalesky et al. . |
| 5,505,709 | 4/1996 | Funderburk et al. . |
| 5,545,152 | 8/1996 | Funderburk et al. . |
| 5,549,574 | 8/1996 | Townsend . |
| 5,554,134 | 9/1996 | Bonnichsen . |
| 5,599,323 | 2/1997 | Bonnichsen et al. . |
| 5,611,785 | 3/1997 | Mito et al. . |
| 5,637,095 | 6/1997 | Nason et al. . |
| 5,647,853 | 7/1997 | Feldmann et al. . |
| 5,722,545 | 3/1998 | Rinne . |
| 5,779,675 | 7/1998 | Reilley et al. . |
| 5,947,935 | 9/1999 | Rhinehart et al. . |

FOREIGN PATENT DOCUMENTS

| | | |
|---|---|---|
| 2240694 | 8/1972 | (DE) . |
| 0544653 | 1/1989 | (EP) . |
| 9800157 | 10/1998 | (WO) . |

OTHER PUBLICATIONS

PCT Application PCT/US99/25414, Search Report mailed Feb. 2, 2000.
PCT Application PCT/US99/25413, Search Report mailed Mar. 7, 2000.

*Primary Examiner*—John D. Yasko
(74) *Attorney, Agent, or Firm*—MiniMed Inc.

(57) ABSTRACT

An improved pump is provided for controlled delivery of fluids wherein the pump includes a reservoir and a movable piston. A plunger slide is in removable contact with the movable piston. A motor, is operably coupled to a drive member, such as a drive screw. The motor is disposed in-line with the drive member and the plunger slide. The drive member is operably connected to the plunger slide and is disposed to be substantially enclosed by the plunger slide when the plunger slide is in at least one position. The drive member is adapted to advance the plunger slide in response to operation of the motor.

26 Claims, 14 Drawing Sheets

HIGH FORCE          LOW FORCE

COMPACT PUMP DRIVE SYSTEM

This application claims priority from provisional patent application No. 60/106,237, filed Oct. 29, 1998 and which is incorporated herein by reference.

BACKGROUND OF THE INVENTION

1. Field of the Invention

This invention relates generally to improvements in infusion pumps such as those used for controlled delivery of medication to a patient. More specifically, this invention relates to an improved infusion pump having a modified and space-efficient drive system.

2. Description of the Related Art

Infusion pump devices and systems are relatively well-known in the medical arts, for use in delivering or dispensing a prescribed medication such as insulin to a patient. In one form, such devices comprise a relatively compact pump housing adapted to receive a. syringe or reservoir carrying a prescribed medication for administration to the patient through infusion tubing and an associated catheter or infusion set.

The infusion pump includes a small drive motor connected via a lead screw assembly for motor-driven advancement of a reservoir piston to administer the medication to the user. Programmable controls can operate the drive motor continuously or at periodic intervals to obtain a closely controlled and accurate delivery of the medication over an extended period of time. Such infusion pumps are utilized to administer insulin and other medications, with exemplary pump constructions being shown and described in U.S. Pat. Nos. 4,562,751; 4,678,408; 4,685,903; 5,080,653 and 5,097,122, which are incorporated by reference herein.

Infusion pumps of the general type described above have provided significant advantages and benefits with respect to accurate delivery of medication or other fluids over an extended period of time. The infusion pump can be designed to be extremely compact as well as water resistant, and may thus be adapted to be carried by the user, for example, by means of a belt clip or the like. As a result, important medication can be delivered to the user with precision and in an automated manner, without significant restriction on the user's mobility or life-style, including in some cases the ability to participate in water sports.

These pumps often incorporate a drive system which uses a lead screw coupled to motors. The motors can be of the DC, stepper or solenoid varieties. These drive systems provide an axial displacement of the syringe or reservoir piston thereby dispensing the medication to the user. Powered drive systems are advantageous since they can be electronically controlled to deliver a predetermined amount of medication by means well known in the art.

In the operation of these pump systems, the reservoir piston will be fully advanced when vitually all of the fluid in the reservoir has been dispensed. Correspondingly, the axial displacement of the motor lead screw is also typically fully displaced. In order to insert a new reservoir which is full of fluid, it is necessary to restore the lead screw to its original position. Thus the lead screw will have to be rewound or reset.

DC motors and stepper motors are advantageous over solenoid motors in that the former are typically easier to operate at speeds that allow rewinding the drive system electronically. Solenoid based drive systems, on the other hand, often must be reset manually, which in turn makes water resistant construction of the pump housing more difficult.

Lead screw drive systems commonly use several gears which are external to the motor. FIG. 1 shows such a lead screw arrangement which is known in the art. A motor 101 drives a lead screw 102 which has threads which are engaged with a drive nut 103. Thus the rotational force of the lead screw 102 is transferred to the drive nut 103 which causes it to move in an axial direction d. Because the drive nut 103 is fixably attached to a reservoir piston 104, it likewise will be forced in an axial direction d', parallel to direction d, thus dispensing the fluid from the reservoir 105 into the infusion set 106. The entire assembly can be contained in a water resistant housing 107.

FIG. 2 shows a different lead screw arrangement which also is known in the art. In this arrangement, a motor 201 (or a motor with an attached gear box) has a drive shaft 201a which drives a set of gears 202. The torque is then transferred from the gears 202 to a lead screw 203. The threads of the lead screw 203 are engaged with threads [not shown] in a plunger slide 204. Thus the torque of the lead screw 203 is transferred to the slide 204 which causes it to move in an axial direction d', parallel to the drive shaft 201a of the motor 201. The slide 204 is in contact with a reservoir piston 205 which likewise will be forced to travel in the axial direction d' thus dispensing fluid from the reservoir 206 into the infusion set 207. The assembly can be contained in a water resistant housing 208.

As previously noted, these lead screw drive systems use gears which are external to the motor. The gears are in combination with a lead screw with external threads which is used to drive the reservoir's piston. This external arrangement occupies a substantial volume which can increase the overall size of the pump. Moreover, as the number of drive components, such as gears and lead screw, increases, the torque required to overcome inherent mechanical inefficiencies can also increase. As a result, a motor having sufficient torque also often has a consequent demand for increased electrical power.

Yet another known drive is depicted in FIGS. 3a and 3b. A reservoir 301 fits into the unit's housing 302. Also shown are the piston member 303 which is comprised of an elongated member with a substantially circular piston head 304 for displacing the fluid in the reservoir 301 when driven by the rotating drive screw 305 on the shaft (not visible) of the drive motor 306.

As is more clearly shown in FIG. 3b, the reservoir 301, piston head 304 and piston member 303 comprise an integrated unit which is placed into the housing 302 (FIG. 3a).

The circular piston head 304 displaces fluid in the reservoir upon axial motion of the piston member 303. The rearward portion of the piston member 303 is shaped like a longitudinal segment of a cylinder as shown in FIG. 3b and is internally threaded so that it may be inserted into a position of engagement with the drive screw 305. The drive screw 305 is a threaded screw gear of a diameter to mesh with the internal threads of the piston member 303. Thus the motor 306 rotates the drive screw 305 which engages the threads of the piston member 303 to displace the piston head 304 in an axial direction d.

While the in-line drive system of FIG. 3a achieves a more compact physical pump size, there are problems associated with the design. The reservoir, piston head and threaded piston member constitute an integrated unit. Thus when the medication is depleted, the unit must be replaced. This results in a relatively expensive disposable item due to the number of components which go into its construction.

Moreover the design of FIG. 3a is not water resistant. Because the reservoir, piston head and threaded piston member are removable, the drive screw 305 and motor 306 are exposed to the atmosphere. Any water which might come in contact with the drive screw 305 and motor 306 will result in corrosion and probable motor failure.

The design of FIG. 3a further gives rise to problems associated with position detection of the piston head 304. The piston member 303 can be decoupled from the drive screw 305. However, when another reservoir assembly is inserted, it is not known by the system whether the piston head 304 is in the fully retracted position or in some intermediate position. Complications therefore are presented with respect to providing an ability to electronically detect the position of the piston head 304 in order to determine the extent to which the medication in reservoir 301 has been depleted.

The construction of pumps to be water resistant give rise to operational problems. As the user travels from various elevations, such as might occur when traveling in an air plane, or as the user engages in other activities which expose the pump to changing atmospheric pressures, differential pressures can arise between the interior of the air tight/water-resistant pump housing and the atmosphere. Should the pressure in the housing exceed external atmospheric pressure, the resulting forces could cause the reservoir piston to be driven inward thus delivering unwanted medication.

Thus it is desirable to have an improved, compact, water resistant drive system which permits safe user activity among various atmospheric pressures. Moreover it is desirable that such a system employ inexpensive medication reservoirs.

SUMMARY OF THE PREFERRED EMBODIMENTS

An improved pump is provided with a reservoir for accommodation of a liquid and a movable piston for varying the size of the reservoir and adapted to discharge the liquid from the reservoir through the outlet. In a certain aspect of the present inventions, a plunger slide is releasably coupled with the movable piston and has at least two positions. A driving device, such as a motor, is operably coupled to a drive member, such as a drive screw. The motor is disposed in-line with the drive screw and the plunger slide. The drive screw is operably connected to the plunger slide and is disposed to be substantially enclosed by the plunger slide when it is in at least one position. The drive screw is adapted to advance the plunger slide in response to operation of the motor.

In one alternative, a housing for the reservoir, the movable piston, the plunger slide, the drive screw and the motor is provided along with a sealing device, such as an O-ring, that separates the portion of the housing which encloses the movable piston from the portion of the housing which encloses the drive screw and the motor.

In another preferred embodiment, a coupler is attached to the plunger slide. The coupler is removably attached to the movable piston to prevent separation of the movable piston from the plunger slide when the air pressure in the housing exceeds the pressure external to the water resistant housing.

In still another embodiment, the housing includes a vent port between the exterior and interior of the housing. The vent port contains a hydrophobic material or a relief valve, either of which will permit air to pass through the vent, but will prevent water from passing.

In another alternative, the driving device is a motor which is attached to the housing with a compliance mount. In another embodiment, the plunger slide comprises a telescoping lead screw formed from at least two segments.

In yet another embodiment, the pump includes a key which is coupled with the plunger slide and which is operable to permit movement of the plunger slide in the direction of the at least two positions but prevent movement of the plunger slide in any other direction.

BRIEF DESCRIPTION OF THE DRAWINGS

FIG. 3b shows the details of a disposable reservoir with the piston and drive member withdrawn of the lead-screw drive mechanism of FIG. 3a.

DETAILED DESCRIPTION OF THE PREFERRED EMBODIMENTS

Figure 1:
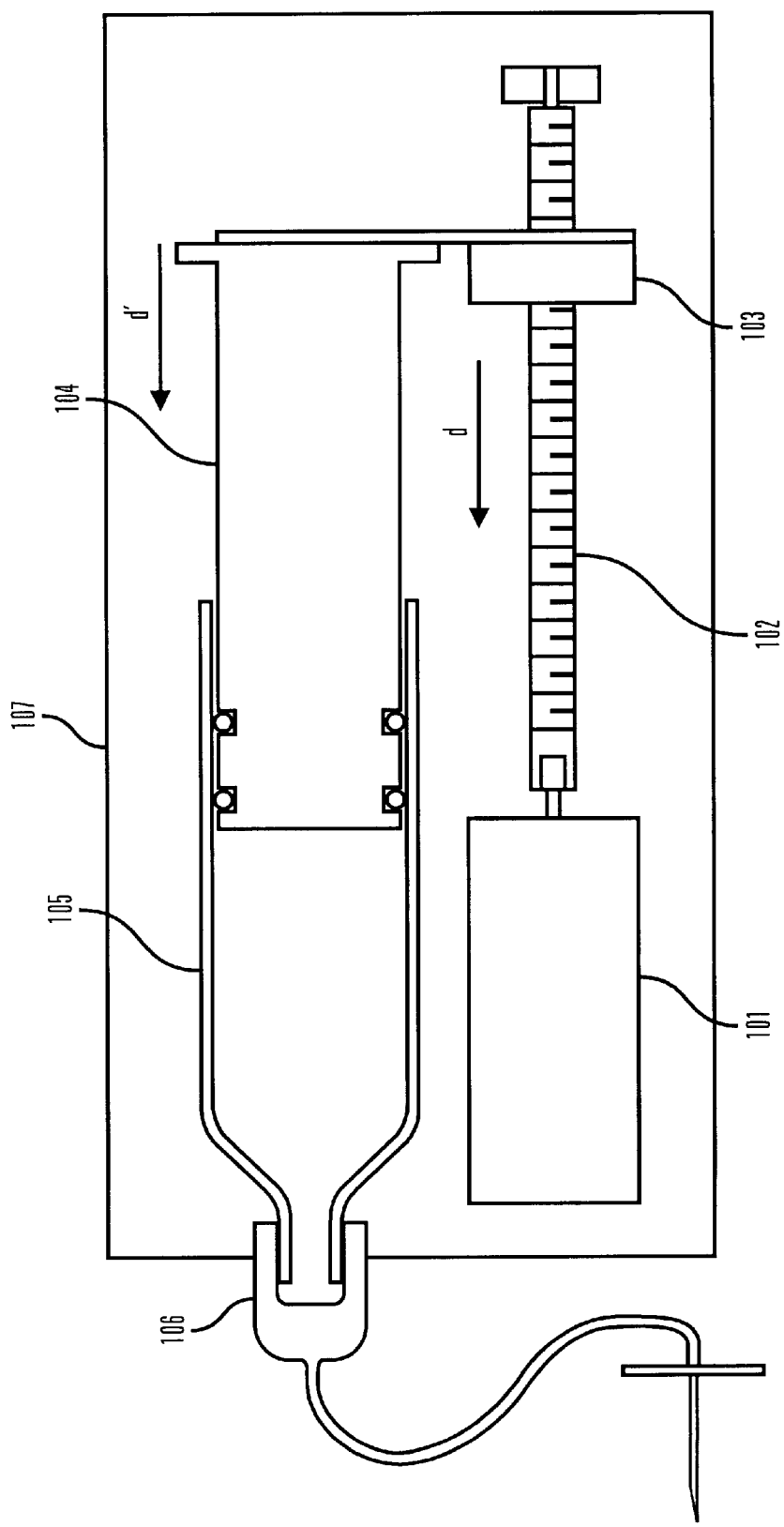
FIG. 1 is a side plan view of a conventional lead-screw drive mechanism.
Figure 2:
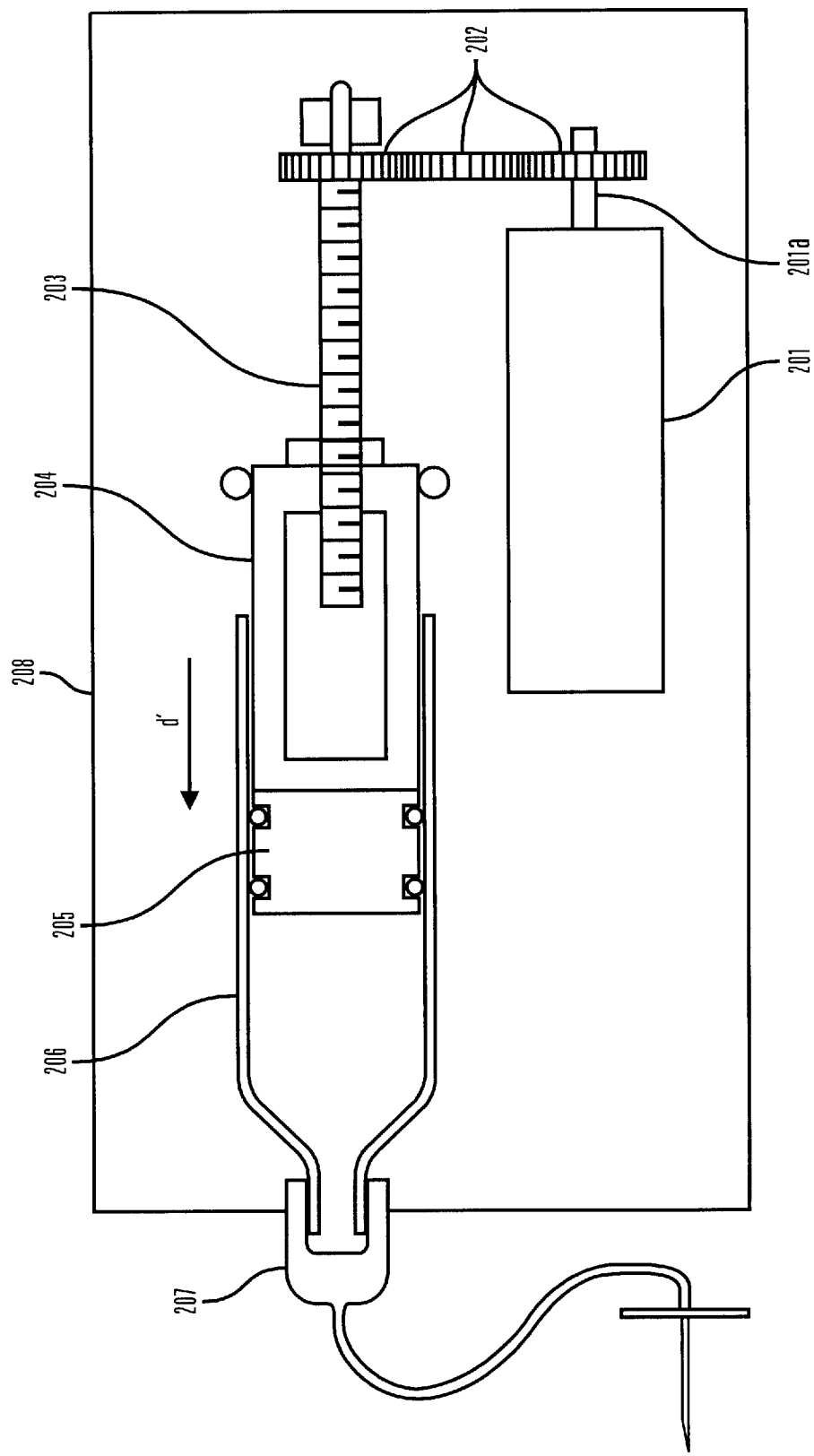
FIG. 2 is a side plan view of a another conventional lead-screw drive mechanism.
Figure 3A:
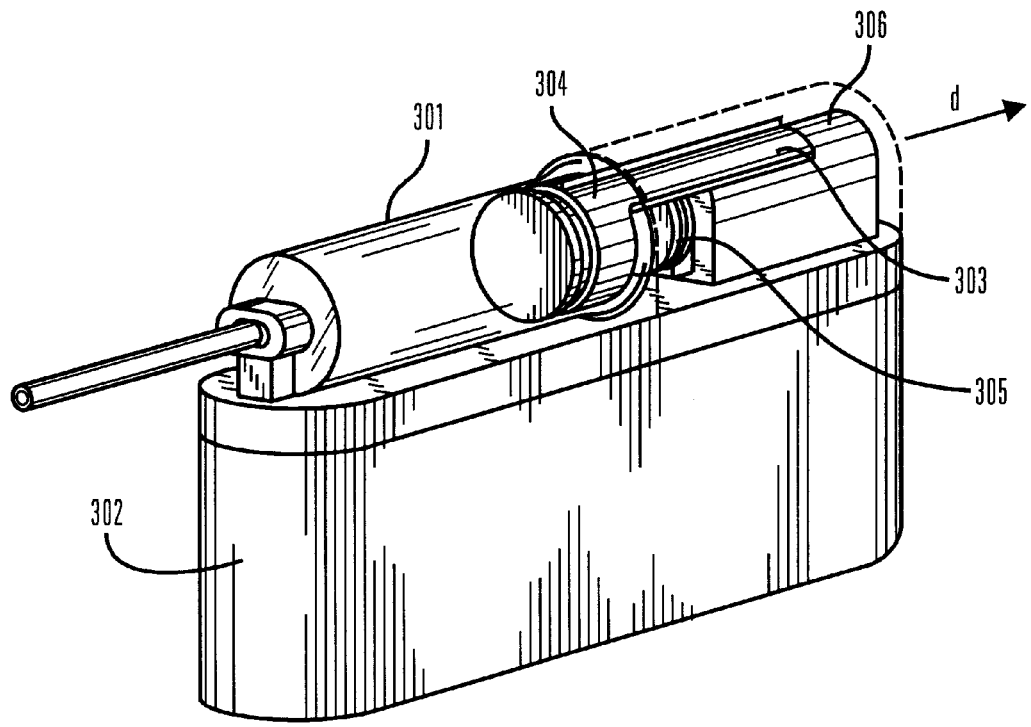
FIG. 3a is a perspective view of another conventional lead-screw drive mechanism.
Figure 3B:
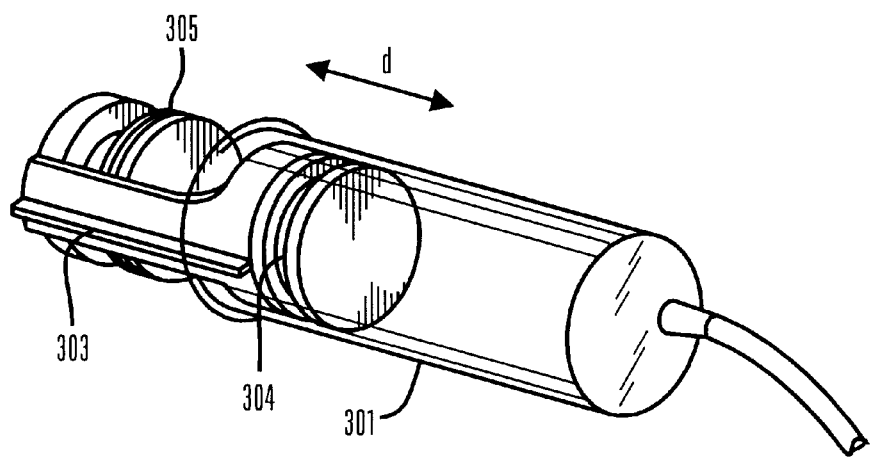

In the following description, reference is made to the accompanying drawings which form a part hereof and which illustrate several embodiments of the present inventions. It is understood that other embodiments may be utilized and structural and operational changes may be made without departing from the scope of the present inventions.

As shown in the drawings for purposes of illustration, some aspects of the present inventions are directed to a drive mechanism for an infusion pump for medication or other fluids. In preferred embodiments, a releasable coupler couples an in-line drive to a plunger or piston of a reservoir to dispense fluids, such as medications, drugs, vitamins, vaccines, hormones, water or the like. However, it will be recognized that further embodiments of the invention may be used in other devices that require compact and accurate drive mechanisms.

In addition, other embodiments use a telescoping drive member (or lead screw) to minimize the packaging dimensions of the drive mechanism and the overall configuration of the medication pump. Still further, a ventilation feature using hydrophobic materials or a relief valve can be employed to equalized any pressure differentials which might otherwise exist between the atmosphere and the interior of the pump housing. As a back up to this ventilation feature, a threaded attachment permits a secure coupling between the reservoir piston and the in-line drive.

Figure 4:
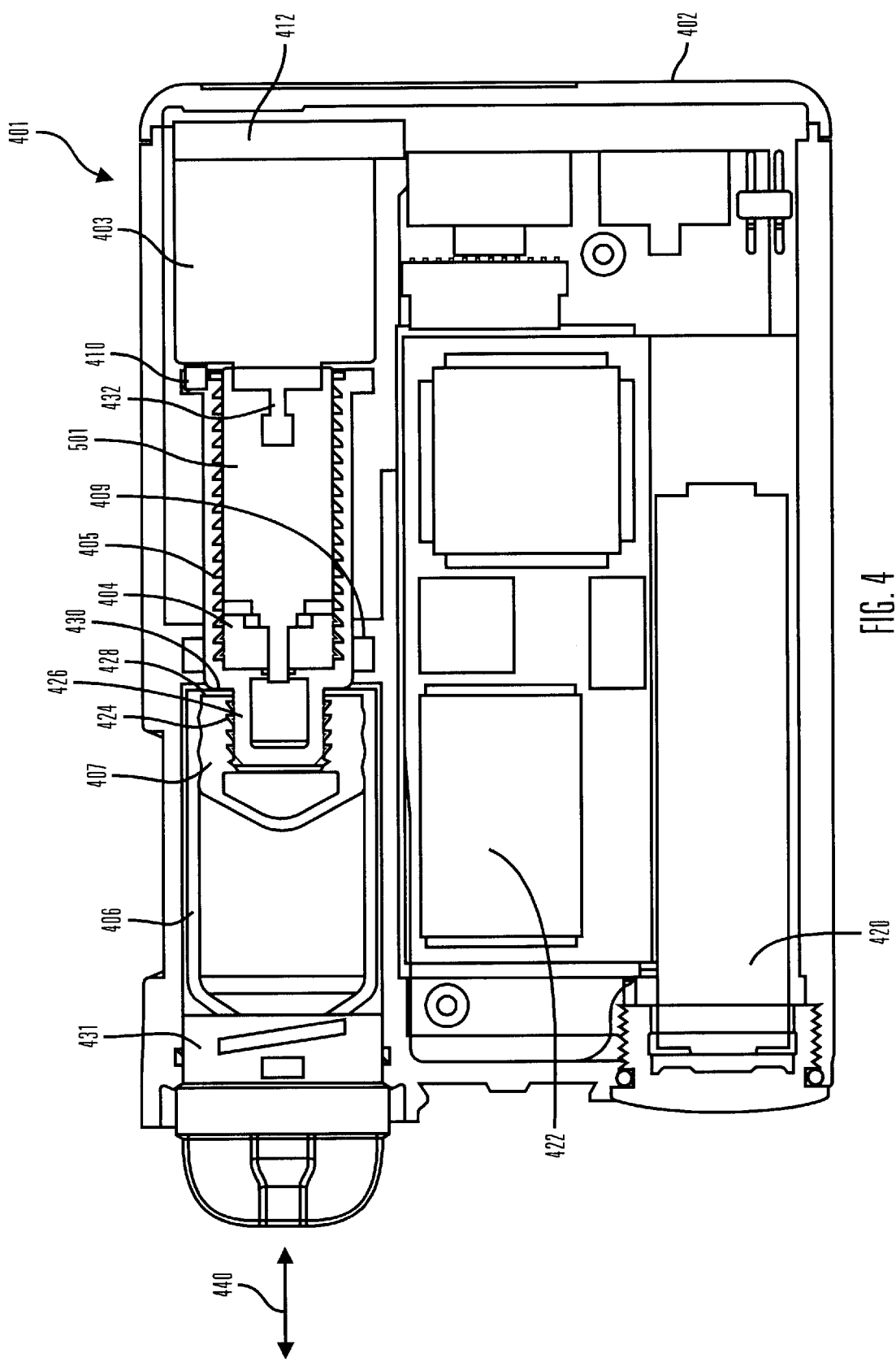
FIG. 4 is a side plan, cut-away view of a drive mechanism in a retracted position in accordance with an embodiment of the present invention.

FIG. 4 shows a side plan, cut-away view of an infusion pump drive mechanism according to a preferred embodiment of the inventions, in which a housing 401, containing a lower section 402 for a power supply 420 and electronic control circuitry 422, accommodates a driving device, such as a motor 403 (e.g., a solenoid, stepper or d.c. motor), a first drive member, such as an externally threaded drive gear or screw 404, a second drive member, such as an internally threaded plunger gear or slide 405, and a removable vial or reservoir 406. The reservoir 406 includes a plunger or piston 407 with O-rings or integral raised ridges for forming a water and air tight seal. The reservoir 406 is secured into the housing 401 with a connector 431 which also serves as the interface between the reservoir 406 and the infusion set tubing (not shown). In a preferred embodiment, the reservoir piston 407 is coupled to the plunger slide 405 by a releasable coupler. In the illustrated embodiment, the coupler includes a female portion 424 which receives a male portion 426 carried by the plunger slide 405. The female portion 424 is positioned at the end face 428 of the piston 407 and includes a threaded cavity which engages the threads of a male screw extending from the end 430 of the plunger slide 405.

While preferred embodiments of the present inventions are directed to disposable, pre-filled reservoirs, alternative embodiments may use refillable cartridges, syringes or the like. The cartridge can be pre-filled with insulin (or other drug or fluid) and inserted into the pump. Alternatively, the cartridge could be filled by the user using an adapter handle on the syringe-piston. After being filled, the handle is removed (such as by unscrewing the handle) so that the cartridge can be placed into the pump.

Referring again to FIG. 4, as the drive shaft 432 of the motor 403 rotates, the drive screw 404 drives the plunger slide 405 directly to obtain the axial displacement against the reservoir piston 407 to deliver the predetermined amount of medication or liquid. When using a DC or stepper motor, the motor can be rapidly rewound when the reservoir is emptied or as programmed by the user. A sealing device, such as an O-ring seal 409 is in contact with the plunger slide 405 thus allowing it to move axially while maintaining a water resistant barrier between the cavity holding the reservoir 406 and the motor 403. This prevents fluids and other contaminants from entering the drive system.

An anti-rotation key 410 is affixed to the plunger slide 405 and is sized to fit within a groove (not shown) axially disposed in the housing 401. This arrangement serves to prevent motor and plunger slide rotation which might otherwise result from the torque generated by the motor 403 in the event that the friction of the O-ring seal 409 is not sufficient alone to prevent rotation.

The motor 403 is a conventional motor, such as a DC or stepper motor, and is journal mounted in the housing 401 by a system compliance mounting 412. A system compliance mount can be useful in aiding motor startup. Certain types of motors, such as stepper motors, may require a great deal of torque to initiate rotor motion when the rotor's initial at-rest position is in certain orientations with respect to the motor's housing. A motor which is rigidly mounted may not have enough power to develop the necessary starting torque. Including system compliance mounting permits the motor housing to turn slightly in response to high motor torque. This alters the orientation between the rotor and the housing such that less torque is required to initiate rotor motion. A compliance mount can include a rubberized mounting bracket. Alternatively, the mounting could be accomplished using a shaft bearing and leaf spring or other known compliance mountings.

Figure 5:
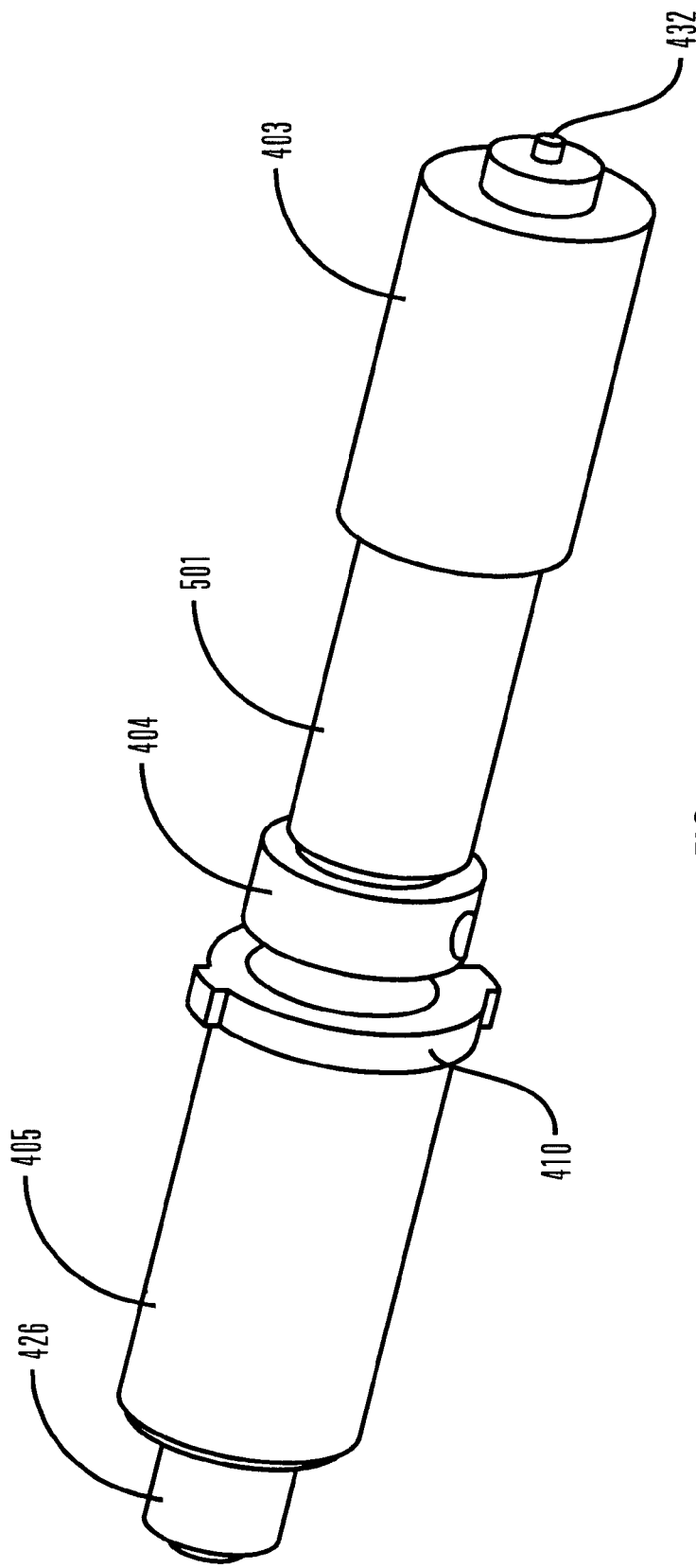
FIG. 5 is a perspective view of the in-line drive mechanism of FIG. 4 outside of the housing.

FIG. 5 shows a perspective view of the in-line drive mechanism of FIG. 4 outside of the housing. The plunger slide 405 (internal threads not shown) is cylindrically shaped and has the screw-shaped male portion 426 of the coupler attached to one end thereof. The anti-rotation key 410 is affixed to the opposite end of the slide 405. The drive screw 404 is of such a diameter as to fit within and engage the internal threads of the plunger slide 405 as shown in FIG. 4. A conventional gear box 501 couples the drive screw 404 to the drive shaft 432 of the motor 403.

Figure 6:
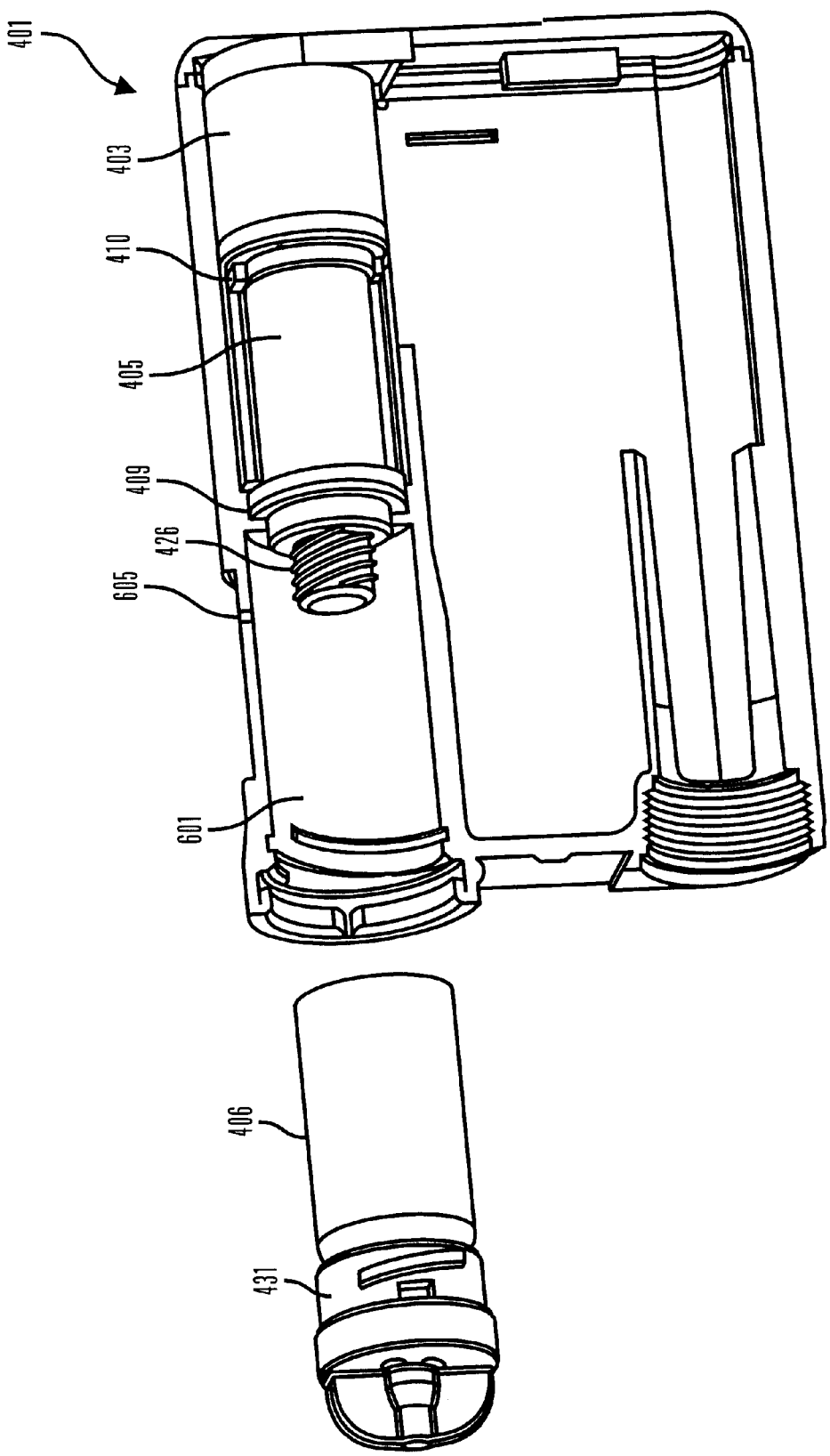
FIG. 6 is a cut-away perspective view of the drive mechanism of FIG. 4 in a retracted position.

FIGS. 4 and 6 show the infusion pump assembly with the plunger slide 405 in the retracted position. The reservoir 406 which may be full of medication or other fluid is inserted in a reservoir cavity 601 which is sized to receive a reservoir or vial. In the retracted position, the plunger slide 405 encloses the gear box 501 (not visible in FIG. 6) while the drive screw 404 (not visible in FIG. 6) remains enclosed within the plunger slide 405 but is situated close to the coupler.

The motor 403 may optionally include an encoder (not shown) which in conjunction with the system electronics can monitor the number of motor rotations. This in turn can be used to accurately determine the position of the plunger slide 405 thus providing information relating to the amount of fluid dispensed from the reservoir 406.

Figure 7A:
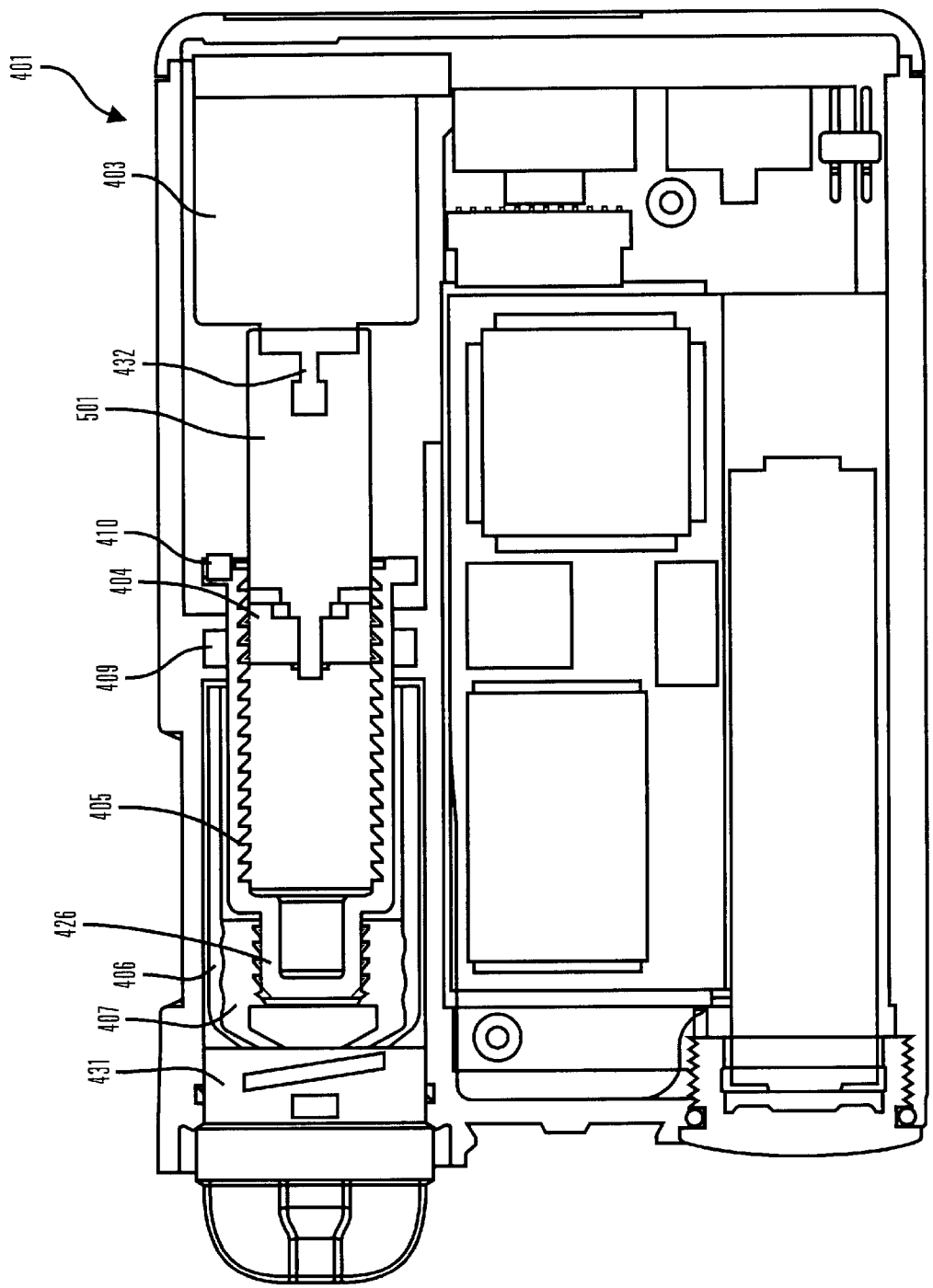
FIG. 7a is a side plan, cut-away view of the drive mechanism of FIG. 4 in an extended position.
Figure 7B:
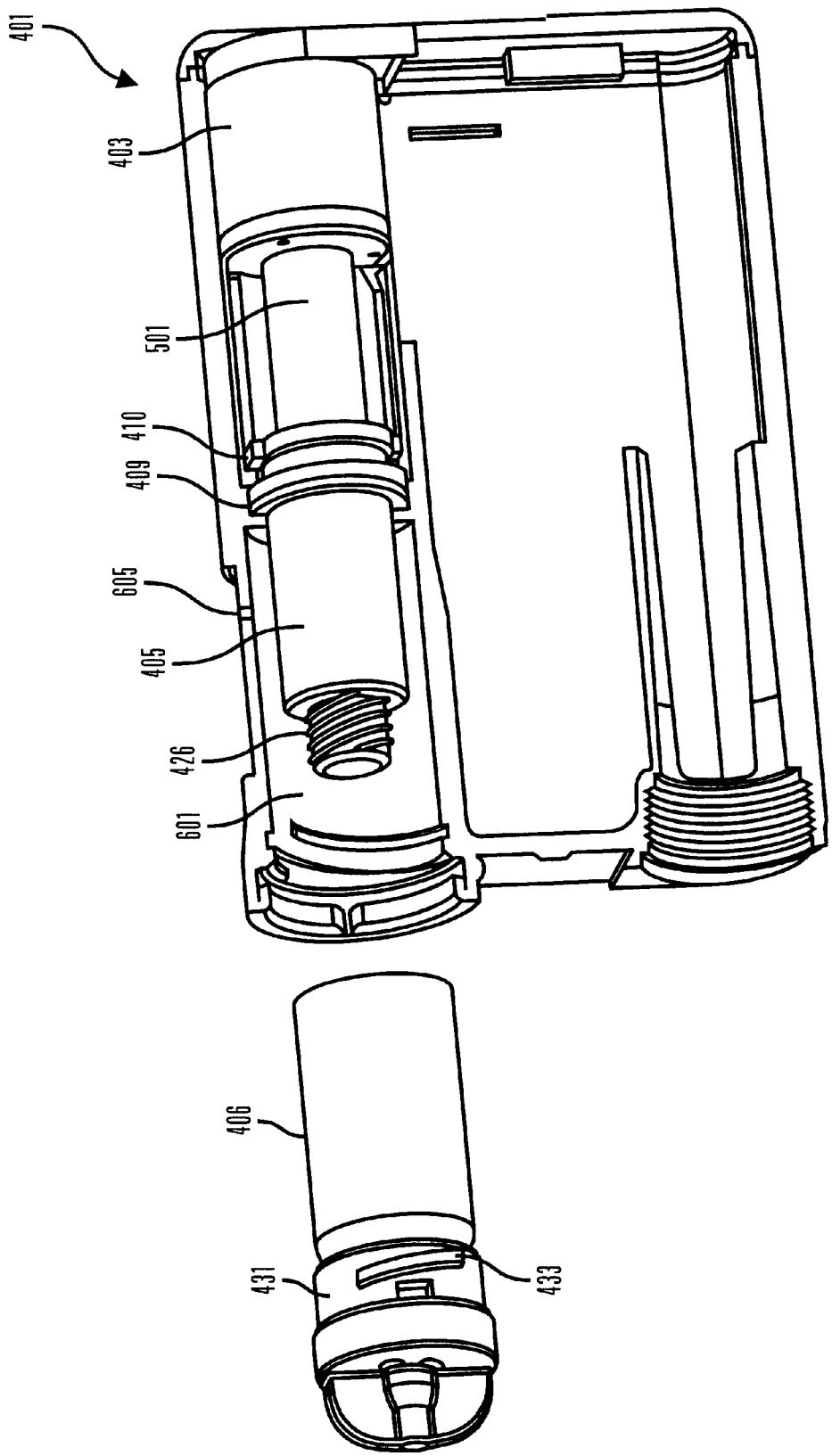
FIG. 7b is a cut-away perspective view of the drive mechanism of FIG. 4 in an extended position.

FIGS. 7a and 7b show the infusion pump assembly with the plunger slide 405 in the fully extended position. In this position, the plunger slide 405 has withdrawn from over the gear box 501 and advanced into the reservoir 406 behind the reservoir piston 407. Accordingly, the plunger slide 405 is sized to fit within the housing of the reservoir 406, such that when the reservoir piston 407 and the plunger slide 405 are in the fully extended position as shown, the reservoir piston 407 has forced most, if not all, of the liquid out of the reservoir 406. As explained in greater detail below, once the reservoir piston 407 has reached the end of its travel path indicating that the reservoir has been depleted, the reservoir 406 may be removed by twisting such that the threaded reservoir piston 407 (not shown in FIG. 7b) disengages from the male portion 426 of the coupler.

In a preferred embodiment, the motor drive shaft 432, gear box 501, drive screw 404, and plunger slide 405 are all coaxially centered within the axis of travel 440 (FIG. 4) of the reservoir piston 407. In certain of the alternative embodiments, one or more of these components may be offset from the center of the axis of travel 440 and yet remain aligned with the axis of travel which has a length which extends the length of the reservoir 406.

Figure 8:
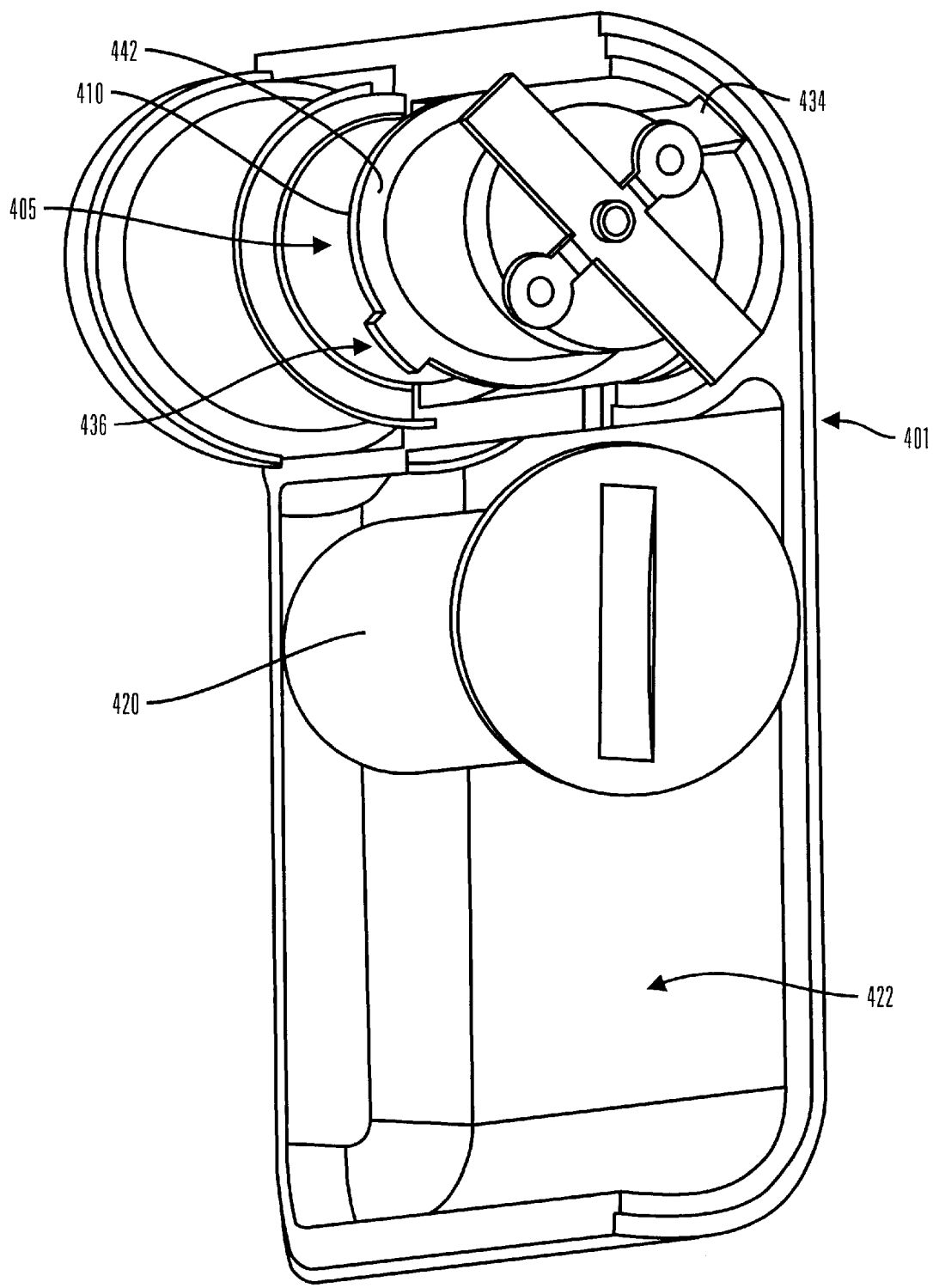
FIG. 8 is a cut-away perspective view of an anti-rotation device for use with the drive mechanism shown in FIG. 4.

FIG. 8 is a cut away perspective view of an anti-rotation device. The anti-rotation key 410 consists of a ring or collar 442 with two rectangular tabs 436 which are spaced 180° apart. Only one tab is visible in FIG. 8. The ring portion 442 of the key 410 surrounds and is attached to the end of the plunger slide 405 which is closest to the motor. Disposed in the housing 401 are two anti-rotation slots 434, only one of which is visible in FIG. 8. The anti-rotation slots 434 are sized to accept the rectangular tabs of the key 410. As the plunger slide 405 moves axially in response to the motor torque as previously described, the slots 434 will permit the key 410 to likewise move axially. However the slots 434 and the tabs 436 of the key 410 will prevent any twisting of the plunger slide 405 which might otherwise result from the torque generated by the motor.

Figure 9:
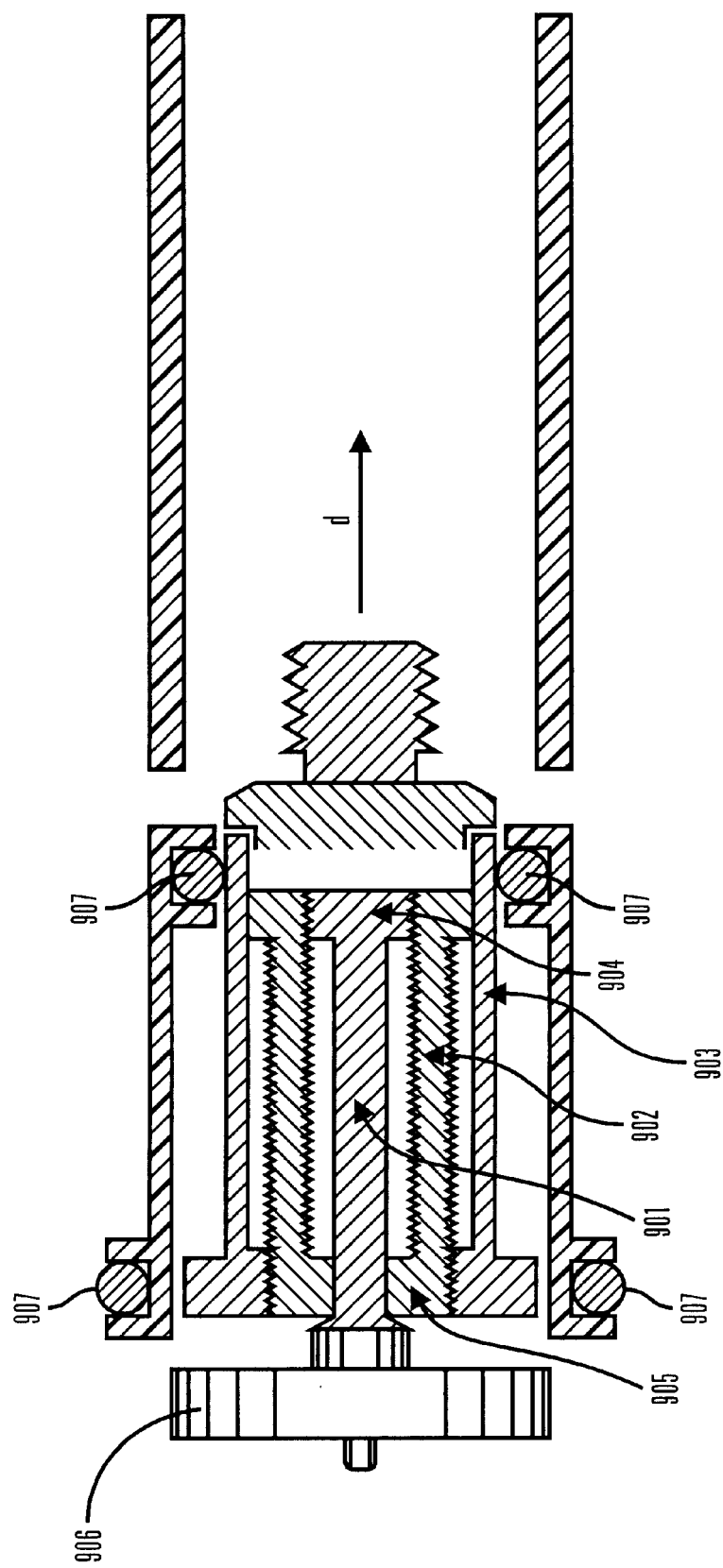
FIG. 9 is a cross-sectional view of a segmented (or telescoping) lead screw in accordance with an embodiment of the present invention.

FIG. 9 illustrates a split lead-screw (or plunger slide) design in accordance with an embodiment of the present inventions. The use of a split lead-screw or telescoping lead screw allows the use of an even smaller housing for the drive mechanism. A telescoping lead-screw formed from multiple segments allows the pump to minimize the dimensions of the drive mechanism, in either in-line or gear driven drive mechanisms.

In preferred embodiments, an interior shaft 901 is rotated by a gear 906 which is coupled to a drive motor (not shown). This in turn extends a middle drive segment 902 by engaging with the threads of an internal segment 904. The middle segment 902 carries an outer segment 903 forward with it in direction d as it is extended to deliver fluid. When the middle segment 902 is fully extended, the internal segment 904 engages with a stop 905 on the middle segment 902 and locks it down from pressure with the threads between the middle and internal segments. The locked middle segment 902 then rotates relative to the outer segment 903 and the threads between the middle segment 902 and the outer segment 903 engage to extend the outer segment 903 in direction d to its full length.

The use of multiple segments is not limited to two or three segments; more may be used. The use of three segments reduces the length of the retracted lead-screw portion of the drive mechanism by half. In alternative embodiments, the outer segment may be connected to the motor and the inner segment may be the floating segment. In preferred embodiments, O-rings 907 are used to seal each segment relative to the other and to form a seal with the housing to maintain water sealing and integrity.

As previously noted, the construction of these pumps to be water resistant can give rise to operational problems. As the user engages in activities which expose the pump to varying atmospheric pressures, differential pressures can arise between the interior of the air tight/water-resistant housing and the atmosphere. Should the pressure in the housing exceed external atmospheric pressure, the resulting forces could cause the reservoir piston to be driven inward thus delivering unwanted medication. On the other hand, should the external atmospheric pressure exceed the pressure in the housing, then the pump motor will have to work harder to advance the reservoir piston.

To address this problem, a preferred embodiment of the inventions includes a venting port which resists the intrusion of moisture. Referring to FIG. 7b, venting is accomplished through the housing 401 into the reservoir cavity 601 via a vent port 605. The vent port can be enclosed by a relief valve (not shown) or covered with hydrophobic material. Hydrophobic material permits air to pass through the material while resisting the passage of water or other liquids from doing so, thus permitting water resistant venting. The preferred embodiment uses a hydrophobic material such as Gore-Tex®, PTFE, HDPE, UHMW polymers from sources such as W.I. Gore & Associates, Flagstaff, Az., Porex Technologies, Fairbum, Ga., or DeWAL Industries, Saunderstown, R.I.. It is appreciated that other hydrophobic materials may be used as well.

Figure 10A:
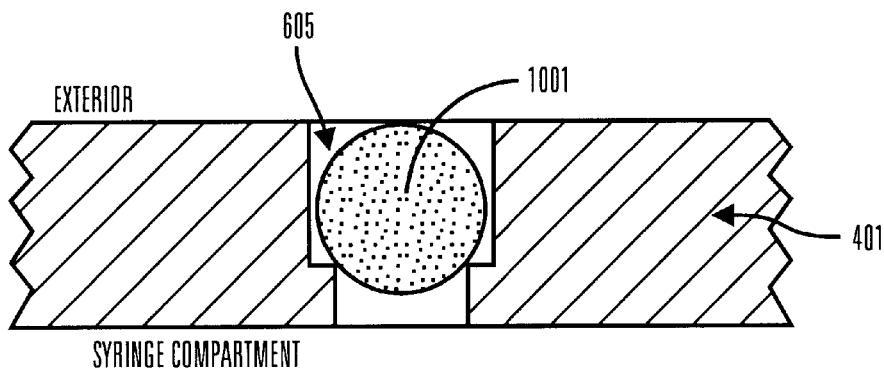
FIGS. 10a, 10b and 10c are cross-sectional views of various embodiments of venting ports for use with the drive mechanism of FIG. 4.
Figure 10B:
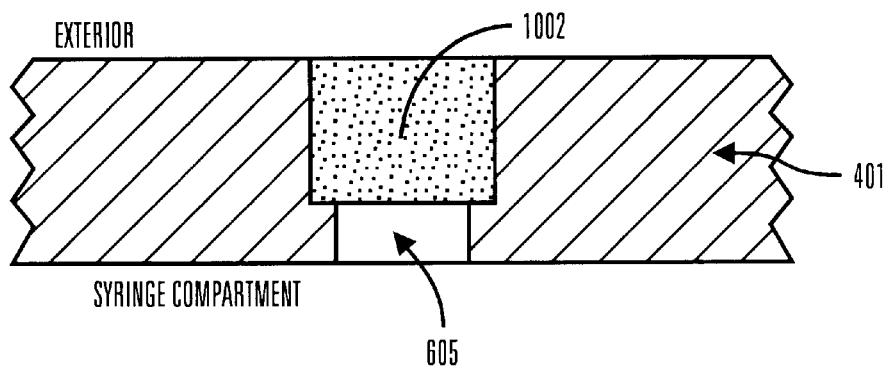
Figure 10C:
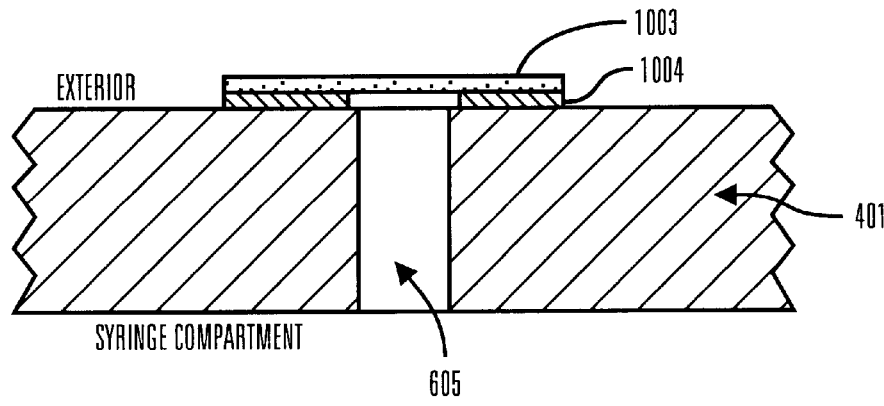

These materials are available in sheet form or molded (press and sintered) in a geometry of choice. Referring to FIGS. 10a–10c, preferred methods to attach this material to the housing 401 include molding the hydrophobic material into a sphere 1001 (FIG. 10a) or a cylinder 1002 (FIG. 10b) and pressing it into a cavity in the pre-molded plastic housing. Alternatively, a label 1003 (FIG. 10c) of this material could be made with either a transfer adhesive or heat bond material 1004 so that the label could be applied over the vent port 605. Alternatively, the label could be sonically welded to the housing. In either method, air will be able to pass freely, but water will not.

In an alternative embodiment (not shown), the vent port could be placed in the connector 431 which secures the reservoir 406 to the housing 401 and which also serves to secure and connect the reservoir 406 to the infusion set tubing (not shown). As described in greater detail in copending application Ser. No. 09/428,818 filed contemporaneously herewith (Attorney docket No. 0059-0307), which application is incorporated by reference in its entirety, the connector and infusion set refers to the tubing and apparatus which connects the outlet of the reservoir to the user of a medication infusion pump.

An advantage of placing the vent port and hydrophobic material in this location, as opposed to the housing 401, is that the infusion set is disposable and is replaced frequently with each new reservoir or vial of medication. Thus new hydrophobic material is frequently placed into service. This provides enhanced ventilation as compared with the placement of hydrophobic material in the housing 401. Material in this location will not be replaced as often and thus is subject to dirt or oil build up which will retard ventilation. In yet another alternative embodiment however, vent ports with hydrophobic material could be placed in both the pump housing and in the connector portion of the infusion set.

Figure 11:
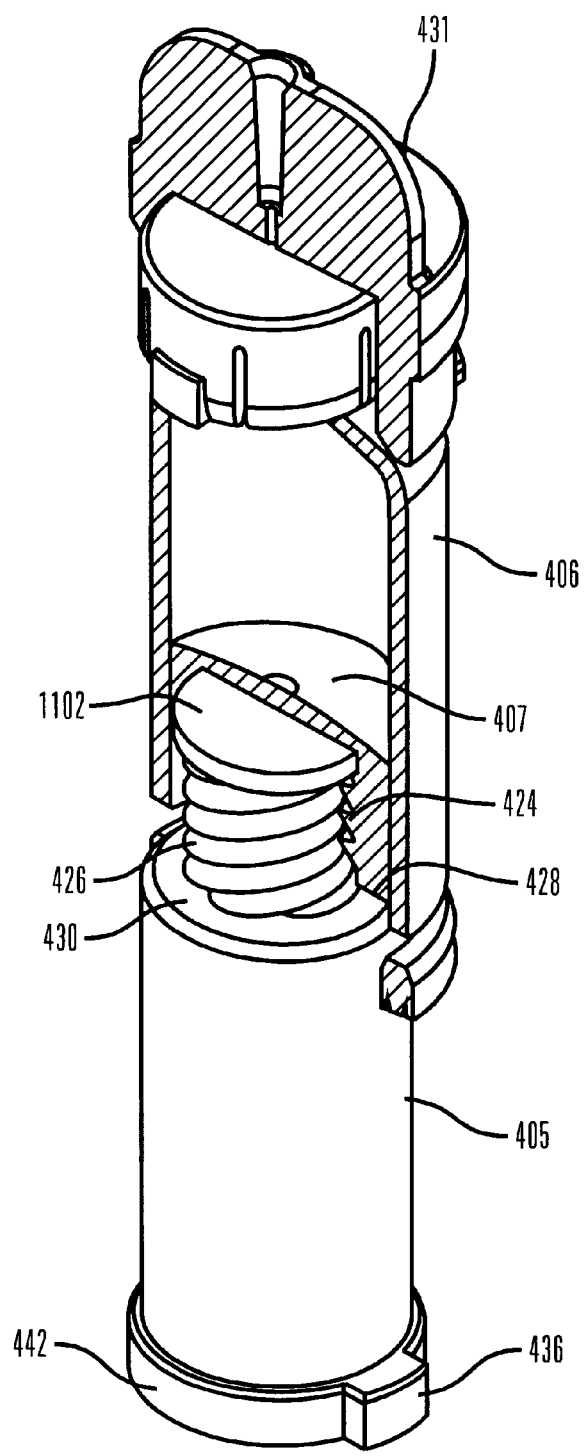
FIG. 11 is a partial, cross-sectional view of a reservoir and plunger slide assembly.

Regardless of the location of the vent port, there remains the possibility that the vent port can become clogged by the accumulation of dirt, oil, etc. over the hydrophobic material. In another feature of certain embodiments of the present invention, the releasable coupler can act to prevent unintentional medication delivery in those instances when the internal pump housing pressure exceeds atmospheric pressure. Referring to FIG. 11, the coupler includes threads formed in a cavity within the external face of the reservoir piston 407. The threaded cavity 424 engages the threads of the male portion 426 which in turn is attached to the end 430 of the plunger slide 405.

This thread engagement reduces or prevents the effect of atmospheric pressure differentials acting on the water resistant, air-tight housing 401 (not shown in FIG. 1) from causing inadvertent fluid delivery. The threads of the male portion 426 act to inhibit or prevent separation of the reservoir piston 407 from the plunger slide 405 which, in turn, is secured to the drive screw 404 (not shown in FIG. 1) by engagement of the external threads of the drive screw 404 with the internal threads of the plunger slide 405. As a result, the coupler resists movement of the reservoir piston 407 caused by atmospheric pressure differentials.

When the reservoir 406 is to be removed, it is twisted off of the coupler male portion 426. The system electronics then preferably cause the drive motor 403 to rapidly rewind so that the plunger slide 405 is driven into a fully retracted position (FIGS. 4 and 6). A new reservoir 406, however, may not be full of fluid. Thus the reservoir piston 407 may not be located in the furthest possible position from the reservoir outlet. Should the reservoir piston 407 be in such an intermediate position, then it may not be possible to engage the threads of the male portion 426 of the coupler (which is in a fully retracted position) with those in the female portion 424 of the coupler in the reservoir piston 407 upon initial placement of the reservoir.

In accordance with another feature of certain embodiments, the illustrated embodiment provides for advancement of the plunger slide 405 upon the insertion of a reservoir into the pump housing. The plunger slide 405 advances until it comes into contact with the reservoir piston 407 and the threads of the coupler male portion 426 of the coupler engage the threads in the female portion 424 in the reservoir piston 407. When the threads engage in this fashion in the illustrated embodiment, they do so not by twisting. Rather, they rachet over one another.

In the preferred embodiment, the threads of the coupler male portion 426 have a 5 start, 40 threads per inch ("TPI") pitch or profile while the threads of the coupler female portion 424 have a 2 start, 40 TPI pitch or profile as illustrated in FIG. 11. Thus these differing thread profiles do not allow for normal tooth-to-tooth thread engagement. Rather, there is a cross threaded engagement.

The purpose of this intentional cross threading is to reduce the force necessary to engage the threads as the plunger slide 405 seats into the reservoir piston 407. In addition, the 2 start, 40 TPI threads of the coupler female portion 424 are preferably made from a rubber material to provide a degree of compliance to the threads. On the other hand, the 5 start, 40 TPI threads of the male coupler portion 426 are preferably made of a relatively hard plastic. Other threading arrangements and profiles could be employed resulting in a similar effect.

Figure 13A:
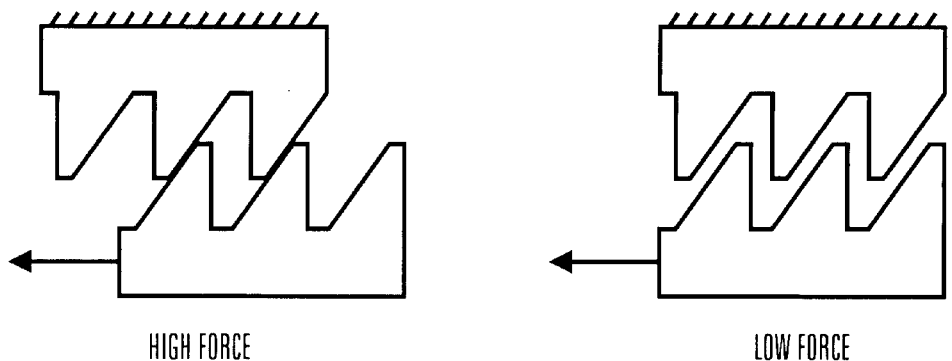
FIGS. 13a and 13b are plunger slide force profile diagrams.
Figure 13A:
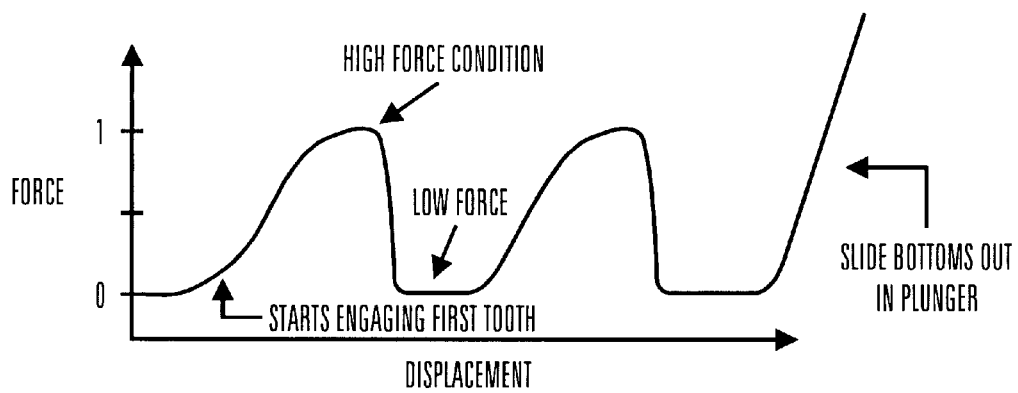

If on the other hand, the threads had a common thread pitch with an equal number of starts given the same degree of thread interference (i.e., the OD of the male feature being larger than the OD of the female feature), then the force needed to insert the male feature would be pulsatile. Referring to FIG. 13a, as each thread tooth engages the next tooth, the insertion force would be high as compared to the point where the thread tooth passes into the valley of the next tooth. But with the cross threaded arrangement of the preferred embodiment, not all of the threads ride over one another at the same time. Rather, they ratchet over one another individually due to the cross-threaded profile. This arrangement results in less force required to engage the threads when the plunger slide moves axially, but still allows the reservoir to easily be removed by a manual twisting action.

While the advantage of utilizing a common thread pitch would be to provide a maximum ability to resist axial separation of the reservoir piston 407 from the plunger slide 405, there are disadvantages. In engaging the threads, the peak force is high and could result in excessive delivery of fluids as the plunger slide 405 moves forward to seat in the cavity of the reservoir piston 407. As described in greater detail in copending application Ser. No. 09/428411 filed contemporaneously herewith (Attorney Docket No. 0059-0308), which application is incorporated by reference in its entirety, the pump may have an occlusion detection system which uses axial force as an indicator of pressure within the reservoir. If so, then a false alarm may be generated during these high force conditions.

Figure 13B:
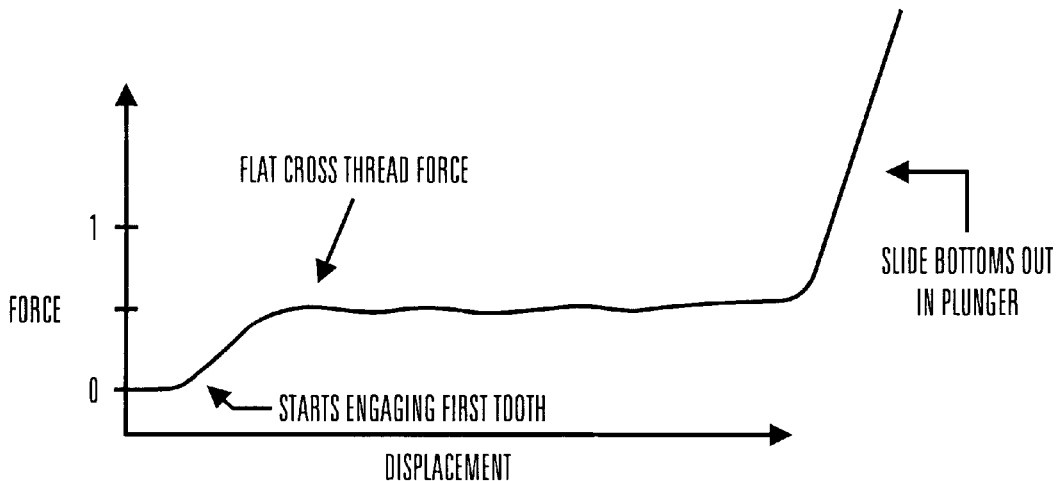

Therefore, the insertion force profile is preferably more flat than that shown in FIG. 13a. To accomplish this, the cross threading design of the preferred embodiment causes the relatively soft rubber teeth of the female portion 424 at the end of the reservoir piston 407 to rachet or swipe around the relatively hard plastic teeth of the coupler resulting in a significantly lower insertion force for the same degree of thread interference. (See FIG. 13b) This is due to the fact that not all of the thread teeth ride over one another simultaneously. Moreover, the cross-sectional shape of the threads are ramped. This makes it easier for the threads to ride over one another as the plunger slide is being inserted into the reservoir piston. However, the flat opposite edge of the thread profile makes it much more difficult for the plunger slide to be separated from the reservoir piston.

Figure 12:
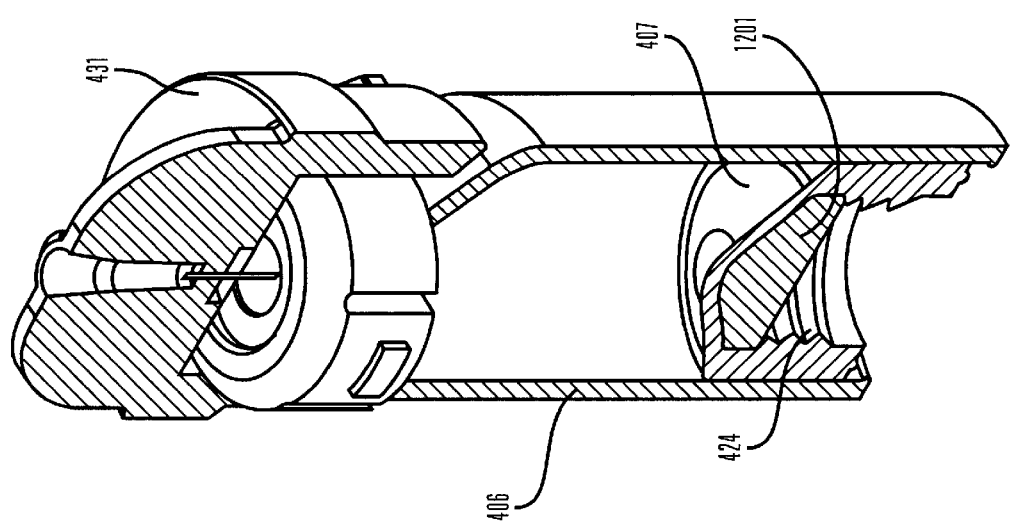
FIG. 12 is a partial, cross sectional view of a reservoir and a reservoir connector.

Referring to FIGS. 11 and 12, the 5 start, 40 TPI (0.125" lead) thread profile of the coupler male portion 426 was chosen in consideration of the thread lead on the preferred embodiment of the connector 431. The connector 431 is secured into the pump housing with threads 433 (FIG. 7b) having a 2 start, 8 TPI (0.250" lead) profile. Therefore the 0.250" lead on the connector is twice that of the reservoir piston 407 which is 0.125". This was chosen to prevent inadvertent fluid delivery during removal of the reservoir from the pump housing, or alternatively, to prevent separation of the reservoir piston 407 from the reservoir 406 during removal from the pump housing. When the connector 431 is disengaged from the pump, the connector 431 as well as the reservoir 406 will both travel with the 0.250" lead. Since the threaded coupler lead is 0.125", the plunger slide 405 will disengage somewhere between the 0.125" lead of the threaded coupler and the 0.250" lead of the infusion set 1103. Therefore, the rate that the reservoir piston 407 is removed from the pump is the same down to half that of the reservoir 406/connector 431. Thus any medication which may be present in the reservoir 406 will not be delivered to the user. Additionally, the length of the reservoir piston 407 is sufficient such that it will always remain attached to the reservoir 406 during removal from the pump. Although the preferred embodiment describes the plunger slide 405 having a coupler male portion 426 with an external thread lead that is different from the connector 431, this is not necessary. The thread leads could be the same or of an increment other than what has been described.

The 2 start thread profile of the coupler female portion 424 on the reservoir piston 407 of the preferred embodiment provides another advantage. Some versions of these reservoirs may be designed to be filled by the user. In such an instance, a handle (not shown) will need to be screwed into the threaded portion of the reservoir piston 407 in order for the user to retract the reservoir piston 407 and fill the reservoir. The number of rotations necessary to fully insert the handle depends upon the distance the handle thread profile travels to fully engage the reservoir piston 407 as well as the thread lead.

For example, a single start, 40 TPI (0.025" lead) thread requires 4 complete rotations to travel a 0.10" thread engagement. However, a 2 start, 40 TPI (0.050" lead) thread only requires 2 complete rotations to travel the 0.10" thread engagement. Therefore, an additional advantage of a 2 start thread as compared to a single start thread (given the same pitch) is that half as many rotations are needed in order to fully seat the handle.

In alternative embodiments which are not shown, the end of the plunger slide 405 may include a detente or ridge to engage with a corresponding formation in the reservoir piston 407 to resist unintended separation of the plunger slide 405 from the reservoir piston 407. In other embodiments, the plunger slide 405 is inserted and removed by overcoming a friction fit. Preferably, the friction fit is secure enough to resist movement of the reservoir piston 407 relative to the plunger slide 405 due to changes in air pressure, but low enough to permit easy removal of the reservoir 406 and its reservoir piston 407 from the plunger slide 405 once the fluid has been expended. In other embodiments, the detente or ridge may be spring loaded or activated to grasp the reservoir piston 407 once the drive mechanism has been moved forward (or extended), but is retracted by a switch or cam when the drive mechanism is in the rearmost (or retracted) position. The spring action could be similar to those used on collets. In other embodiments of the inventions, the threaded coupler may be engaged with the threaded cavity of the reservoir piston by twisting or rotating the reservoir as it is being manually placed into the housing.

As set forth above, the reservoir piston 407 is made of rubber. In the illustrated embodiment, an insert 1201 (FIG. 12) which is made of hard plastic may provided in the upper portion of the reservoir piston 407. The insert 1201 provides stiffness to the rubber reservoir piston 407. This reduces undesirable compliance which is associated with the reservoir. Without the insert 1201, the flexibility in the reservoir piston 407 due to its rubber composition could cause it to deform under varying reservoir fluid back pressures. This deformation could in turn vary the internal volume of the reservoir 406. Such variances may adversely affect the controlled delivery of the fluid from the reservoir 406 via the infusion set to the user.

It can be appreciated that the design of FIGS. 4–12 results in an arrangement where; the plunger slide 405 is reliably but releasably coupled to the drive screw 404. When it is time to replace the reservoir 406, it can be detached from the male end of the coupler without affecting the plunger/drive screw engagement. Moreover in the preferred embodiment, the plunger slide 405 is shaped as a hollow cylinder with internal threads. Thus it completely encircles and engages drive screw 404. When the plunger slide 405 is in a relatively retracted position, it encloses any gears which couple the motor 403 with the drive screw 404 thus achieving an extremely compact design. Alternative embodiments include an arrangement where the plunger slide 405 encloses the motor 403 itself. A vent port covered with hydrophobic material as well as a threaded coupler provide redundant means for permitting exposure of the pump to changing atmospheric pressures without the unintended delivery of medication.

While the description above refers to particular embodiments of the present inventions, it will be understood that many modifications may be made without departing from the spirit thereof. The accompanying claims are intended to cover such modifications as would fall within the true scope and spirit of the present inventions. The presently disclosed embodiments are therefore to be considered in all respects as illustrative and not restrictive, the scope of the inventions being indicated by the appended claims rather than the foregoing description, and all changes which come within the meaning and range of equivalency of the claims are therefore intended to be embraced therein.

What is claimed is:

1. A portable medical device for dispensing liquid from a liquid reservoir having a piston which defines an axis of travel, the medical device comprising:

a drive motor having a rotating drive shaft which defines an axis of rotation, said drive shaft axis of rotation being coaxially aligned with the piston axis of travel;

a gearbox coupled to the drive motor drive shaft;

at least one plunger slider coupled to the gearbox and adapted to translate from a retracted position to an extended position to displace the piston along the piston axis of travel in response to rotation of the drive motor drive shaft wherein the at least one plunger slider substantially radially surrounds at least a portion of a length of the gearbox when the at least one plunger slider is in the retracted position; and a releasable coupler adapted to releasably couple the at least one plunger slider to the piston.

2. The medical device according to claim 1, wherein the medical device includes a first drive gear positioned to be rotatably actuated by the drive motor drive shaft, said first drive gear having internal threads; and wherein the at least one plunger slider includes a second drive gear having external threads positioned to be engaged by the first drive gear internal threads and linearly actuated by rotation of the first drive gear internal threads; and wherein the releasable coupler is adapted to releasably couple the second drive gear to the reservoir piston.

3. The medical device according to claim 1, wherein the medical device includes a first drive gear positioned to be rotatably actuated by the drive motor drive shaft, said first drive gear having external threads; and wherein the at least one plunger slider includes a second drive gear having internal threads positioned to be engaged by the first drive gear external threads and linearly actuated by rotation of the first drive gear external threads; and wherein the releasable coupler is adapted to releasably couple the second drive gear to the reservoir piston.

4. The medical device of claim 3 wherein the second drive gear defines a cavity and the second drive gear internal threads encircle the second drive gear cavity.

5. The medical device of claim 1, wherein the releasable coupler includes a first threaded member carried by the at least one plunger slider and a second threaded member is carried by the reservoir piston and adapted to engage the first threaded member.

6. The medical device of claim 5, wherein the first threaded member comprises a screw extending from the at least one plunger slider and having external threads, and the second threaded member comprises a cavity defined by the reservoir piston and having internal threads positioned to be engaged by the screw external threads.

7. The medical device of claim 6 wherein the external threads of the screw are made of a material having a first hardness and the internal threads of the piston cavity are made of a material having a second hardness.

8. The medical device of claim 6 wherein the external threads of the screw have a first lead and wherein the internal threads of the piston cavity have a second lead.

9. The medical device of claim 4 further comprising a housing enclosing the drive motor, the first and second drive gears, the releasable coupler and the reservoir and wherein the housing further includes a vent port containing a hydrophobic material.

10. The medical device of claim 3 wherein the second drive gear comprises a telescoping lead screw formed from at least two segments.

11. A medical device for dispensing liquid from a liquid reservoir having a piston which defines an axis of travel, the medical device comprising:

a drive motor having a rotating drive shaft which defines an axis of rotation, said drive shaft axis of rotation being coaxially aligned with the piston axis of travel;

a gearbox coupled to the drive motor drive shaft;

a first drive gear positioned to be rotatably actuated by the gearbox said first drive gear having external threads;

a second drive gear having internal threads positioned to be engaged by the first drive gear external threads and linearly actuated from a retracted position to an extended position by rotation of the first drive gear threads;

wherein the second drive gear substantially radially surrounds at least a portion of a length of the gearbox when the second drive gear is in the retracted position; and a releasable coupler means for releasably coupling the second drive gear to the reservoir piston wherein linear actuation of the second drive gear linearly actuates the reservoir piston.

12. A method of dispensing liquid from a portable liquid reservoir having a piston which defines an axis of travel, the method comprising:

coupling a first reservoir piston of a first reservoir to at least one plunger slider;

rotating a motor drive shaft which defines an axis of rotation, said drive shaft axis of rotation being coaxially aligned with the piston axis of travel;

rotating gears in a gearbox with the drive motor drive shaft;

translating the at least one plunger slider from a retracted position to an extended position in response to rotation of the gears in the gearbox to move the reservoir piston along the piston axis of travel using the at least one plunger slider to dispense the liquid from the reservoir; and wherein the at least one plunger slider substantially radially surrounds at least a portion of a length of the gearbox when the plunger slider is in the retracted position; and releasing the first reservoir piston from the at least one plunger slider.

13. The method of claim 12, further comprising coupling a second reservoir piston of a second reservoir to the at least one plunger slider following releasing the first reservoir piston.

14. The method of claim 12, wherein the coupling includes driving a first threaded member carried by the at least one plunger slider into engagement with a second threaded member carried by the reservoir piston.

15. The method of claim 14 wherein the first threaded member comprises a screw extending from the at least one plunger slider and having external threads, and the second threaded member comprises a cavity defined by the piston and having internal threads positioned to be engaged by the screw external threads.

16. The method of claim 15 wherein the external threads of the screw are made of a material having a first hardness and the internal threads of the piston cavity are made of a material having a second hardness.

17. The method of claim 15 wherein the external threads of the screw have a first lead and wherein the internal threads of the piston cavity have a second lead.

18. The method of claim 14 wherein the releasing includes rotating the reservoir piston to unscrew the first threaded member from the second threaded member.

19. The method of claim 12 further comprising venting a housing enclosing the drive motor and linear actuator through a vent port containing a hydrophobic material.

20. A portable medical device for dispensing liquid from a liquid reservoir having a piston which defines an axis of travel, the medical device comprising:

a first drive member;

means for driving the first drive member, said driving means being coaxially aligned with the piston axis of travel;

a second drive member coaxially aligned with the piston axis of travel;

means for linearly actuating the second drive member from a retracted position to an extended position with the first drive member;

wherein the linear actuation of the second drive member linearly actuates the piston, and wherein the second drive member substantially radially surrounds at least a portion of a length of the driving means when the second drive member is in the retracted position; and means for releasably coupling the second drive member with the piston.

21. The medical device of claim 20 further comprising a housing enclosing the first and second drive members, the driving means and the linear actuating means, wherein the housing includes means for venting the housing to the atmosphere without permitting liquids to pass through said venting means.

22. A medical device according to claim 1, wherein the at least one plunger slider substantially radially surrounds at least a portion of a length of the drive motor when the at least one plunger slider is in the retracted position.

23. A medical device according to claim 22, wherein the drive motor includes an encoder.

24. A medical device according to claim 1, wherein the liquid reservoir is rotatably removable from the plunger slider and another liquid reservoir may be used to replace the liquid reservoir, and the at least one plunger slider is permanently coupled to the gearbox.

25. A portable medical device for dispensing liquid from a liquid reservoir having a piston which defines an axis of travel, the medical device comprising:

a solenoid;

a drive shaft mechanically coupled to rotate in response to actuation of the solenoid, and coaxially aligned with the piston axis of travel; and at least one plunger slider coupled to the drive shaft to translate from a retracted position to an extended position to displace the piston along the piston axis of travel and dispense liquid form the reservoir in response to rotation of the drive shaft, wherein the at least one plunger slider substantially radially surrounds at least a portion of a length of the solenoid when the at least one plunger slider is in the retracted position.

26. A medical device according to claim 25, wherein the at least one plunger slider is releasably coupled to the piston.

* * * * *